United States Patent [19]

Batz

[11] 4,394,512
[45] Jul. 19, 1983

[54] 1-(SUBSTITUTED PHENYL) AMINOANTIPYRIN COMPOUNDS

[75] Inventor: Hans-Georg Batz, Tutzing, Fed. Rep. of Germany

[73] Assignee: Boehringer Mannheim GmbH, Mannheim-Waldhof, Fed. Rep. of Germany

[21] Appl. No.: 228,011

[22] Filed: Jan. 23, 1981

[30] Foreign Application Priority Data

Feb. 5, 1980 [DE] Fed. Rep. of Germany ....... 3004129
Oct. 7, 1980 [DE] Fed. Rep. of Germany ....... 3039207
Jan. 13, 1981 [DE] Fed. Rep. of Germany ....... 3100807

[51] Int. Cl.³ .......................................... C07D 231/46
[52] U.S. Cl. ................................... 548/365; 548/366; 435/10
[58] Field of Search ......................... 548/365, 366, 358

[56] References Cited

U.S. PATENT DOCUMENTS 2,281,014  4/1942  Winnek ............................... 548/358
2,993,884  7/1961  Ruegg et al. ........................ 548/358
4,247,631  1/1981  Nix et al. ............................... 435/10

OTHER PUBLICATIONS

Stepnova et al., Chem. Abst. 1975, vol. 83, No. 97119v.
Kugita et al., Chem. Abst. 1970, vol. 73, No. 87914e.

Primary Examiner—John M. Ford
Assistant Examiner—Natalia Harkaway
Attorney, Agent, or Firm—Felfe & Lynch

[57] ABSTRACT

Compounds of the general formula

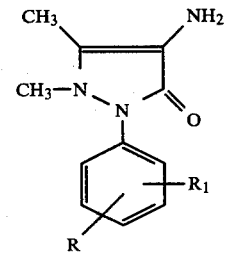

wherein R represents an alkyl group of 1 to 3 carbon atoms or the group $N(R_2)_2$, in which $R_2$ represents a hydrogen atom, an alkyl group of 1 to 3 carbon atoms, or an acyl group of 1 to 3 carbon atoms, and $R_1$ has the same meaning as R or is a hydrogen atom, are new and are suitable as chromogens for measuring $H_2O_2$ formation in enzymatic reactions.

3 Claims, No Drawings

1-(SUBSTITUTED PHENYL) AMINOANTIPYRIN COMPOUNDS

The invention relates to new aminoantipyrin compounds of the general formula

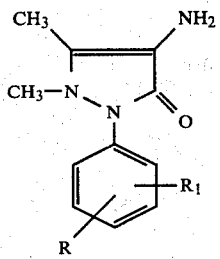

wherein R represents an alkyl group of 1 to 3 carbon atoms or the group $N(R_2)_2$ in which $R_2$ represents a hydrogen atom, an alkyl group of 1 to 3 carbon atoms or an acyl group of 1 to 3 carbon atoms, and $R_1$ has the same meaning as R or is a hydrogen atom, and to their use as chromogens.

Hydrogen peroxide is the reaction product of numerous enzymatic reactions in which oxidases take part. Such reactions, such as for example the oxidation of glycerin by glycerinoxidase or of cholesterol by cholesterinoxidase, are of great importance in analysis, and in this case especially for medical diagnosis.

Known methods for the determination of enzymatically formed $H_2O_2$ are based on titrimetic, potentiometric, polarographic and colorimetric methods, and on enzymatic methods using the enzymes catalase or peroxidase. In enzymatic determinations by means of peroxidase, chromogens are used as indicators which react with hydrogen peroxide in the presence of peroxidase with the formation of a dye which can be determined photometrically. One known such reagent for the $H_2O_2$ determination contains the Trinder indicator system (Ann. clin. Biochem. 6 (1969), 24–27), in which phenol is oxidatively coupled with 4-aminoantipyrin as chromogen, in the presence of peroxidase, by the action of $H_2O_2$, to form a dye which is determined photometrically. Other phenolic compounds can be used instead of phenol.

One disadvantage of 4-aminoantipyrin as chromogen in the above-described hydrogen peroxide determination is in the poor stability of the dye that is formed. Since in test systems it is desirable to measure against the blank value of the reagents, even an apparently slight improvement of the dye stability represents a great advantage with regard to practicability, for example by making it possible to provide longer reading times.

It is therefore the object of the invention to create new compounds which can be used as chromogens in hydrogen peroxide determination instead of 4-aminoantipyrin, and which have better color stabilities in the dyes formed in the oxidative coupling with a phenolic compound.

This object is achieved by the above-described new compounds which are derivatives of 4-aminoantipyrin. In these compounds the substituents R and $R_1$ can assume any position in the phenyl moiety. Compounds in which the moieties R and $R_1$ are in the para and/or ortho position are preferred on account of their easier availability.

The compounds of the invention can be prepared by known methods, for example by the nitration of antipyrin with two equivalents of nitric acid with the formation of dinitroantipyrin and reduction of the nitro groups to the corresponding amino groups, for example by means of zinc dust. The hydrogen atoms of the phenylic amino group can be alkylated with an alkylating agent, such as alkyl iodide, or acylated with an acylating agent, such as acetic acid anhydride, after masking the amino group in position 4 of the antipyrin, for example by forming the Schiff base with benzaldehyde. The derivatives in accordance with the invention, in which R or $R_1$ represents an alkyl group, are best prepared by setting out in a similar manner from the corresponding alkylated phenylpyrazolones.

On the basis of the better color stability of the dyes which are formed by the compounds of the invention in the oxidative coupling with a phenolic compound and hydrogen peroxide and peroxidase, the compounds of the invention are especially suitable for use in methods and reagents for the enzymatic determination of hydrogen peroxide. In this application, the common phenolic compounds can be used which can be coupled with 4-aminoantipyrin with the formation of dye. Examples of other suitable compounds are phenol itself, other phenol derivatives, aniline derivatives, naphthol, naphthol derivatives, naphthylamine, naphthylamine derivatives, aminoquinolines, hydroxyquinolines, dihydroxyphenylacetic acid, and the like. The reaction is performed in buffered solution. Suitable buffer substances and pH values are the substances and conditions known for peroxidase. pH values between 6 and 9 are preferred. Otherwise, the choice of the buffer and of the pH, in the case of a preliminary enzymatic reaction forming hydrogen peroxide, is determined mainly by the requirements with regard to buffer and the pH of the enzymes involved. These conditions are all known to the person skilled in the art and therefore require no further explanation.

A reagent for the determination of hydrogen peroxide, based on peroxidase, at least one compound of the invention, at least one phenolic compound, and buffer, can additionally contain conventional solvents, stabilizers and/or surface active substances. The following quantity ratios of the essential components of this reagent have proven to be especially suitable:

0.5 to 100 U/ml peroxidase, 0.05 to 20 mmol/l compound of the invention, 0.5 to 50 mmol/l phenolic compound.

Surface active agents, if they are used, are used preferably in amounts of 0.001 to 0.1 g/ml of the ready-to-use reagent solution.

The following examples will further explain the invention.

EXAMPLE 1

A. Dinitroantipyrin

Chemicals:
5 g (≅0.0268 mol) antipyrine;
3.7 ml = 3.38 g (≅2×0.0268 mol) 65% $HNO_3$;
36 ml concentration sulfuric acid.

Performance:

Dissolve 5 g of antipyrin in 30 ml of concentrated $H_2SO_4$, add 3.7 ml of concentrated $HNO_3$ and 6 ml of $H_2SO_4$ (antipyrin heats upon dissolving in $H_2SO_4$ to approximately 40° C.), add $HNO_3/H_2SO_4$ drop by drop with ice cooling (max. temperature +10° C.). Then heat slowly and place for 30 minutes on a boiling water bath (mixture becomes increasingly darker), cool, pour onto ice (about 1 liter), remove red precipitate with suction filter, recrystallize from glacial acetic acid.

Yield: 4.9 g.

B. Diaminoantipyrin

Chemicals:
4 g dinitroantipyrin (≅0.0144 mol);
8 g zinc dust (≅0.123 mol).

Performance:

Dissolve 4 g of dinitroantipyrin in 50 ml of concentrated hydrochloric acid with cooling (max. 20° C.), add zinc dust (about 8 g) until solution is colorless. Add 40% NaOH/NaOH tablets to pH 7; thick precipitate forms which is difficult to suction filter (not much more can be extracted with $CHCl_3$). Adjust mother liquor to pH 11.5 with $CHCl_3$, extract, concentrate. Sample dissolves in water, gives a dark red color with $DCP/FeCl_3$.

Yield: 0.4 g.

EXAMPLE 2

A. Preparation of the 4-benzal compound of 1-(p-aminophenyl)-2,3-dimethyl-4-aminopyrazolone-5

(II)

1.09 g (5 mmol) of diaminoantipyrin (I) is dissolved in 15 ml of water and adjusted to pH 10 with 1 N soda lye. 0.53 ml (5 mmol) of benzaldehyde is added. The mixture is stirred vigorously for 20 hours at room temperature. Then the crystalline product is removed with a suction filter and washed with water and ether.

Yield: 82%.

The substance II which is obtained is used without further refining operations for the following reactions.

B. 4-Benzal compound of 1-(p-diethylamino-phenyl)-2,3-dimethyl-4-amino-pyrazolone-5

9.18 g of the 4-benzal compound of diaminoantipyrin (0.03 mol) is dissolved in 250 ml of ethylene glycol dimethyl ether with refluxing. Then the mixture is cooled to 60° C. Then 56 g of potassium carbonate as well as 14.6 ml = 28.0 g of ethyl iodide (0.18 mol) is added. The mixture is then refluxed for 9 hours and the potassium carbonate is removed with a suction filter. The filtrate is vacuum-dried. Residue: 12.16 g. The residue is chromatographed (ethanol) through a silica gel column. The chromatographically purest fractions are crystallized from diethyl ether.

Yield: 3.1 g.

DC Results: Uniform [=chromatographically pure].

C.
1-(p-Diethylamino-phenyl)-2,3-dimethyl-4-amino-pyrazolone-5

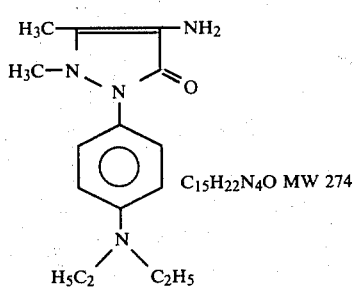

C₁₅H₂₂N₄O MW 274

1.0 g of the product of step 2 is dissolved in 35 ml of hydrochloric acid (2 N) at room temperature and then stirred for 2.5 hours. The BV cleavage is traced by chromatography. The mixture is extracted three times with 30 ml of chloroform each time to separate the benzaldehyde. Then the acid, aqueous phase is adjusted with caustic soda solution (33%) to pH 10.0 and again extracted with chloroform (thrice with 30 ml each time). The chloroform is withdrawn in vacuo. Residue: 0.855 g. The residue is subjected to another silica gel treatment (chloroform/ethanol 1:1).

The yield of chromatographically uniform substance is 0.356 g. MS: 274.

EXAMPLE 3

A. 4-Benzal compound of 1-(p-acetamino-phenyl)-2,3-dimethyl-4-aminopyrazolone-5

15.3 g of benzal compound of diaminoantipyrin (1/20 mol) is dissolved in 60 ml of dimethylformamide at 45° to 50° C. The addition of 10.2 g of acetic anhydride is performed at room temperature, whereupon the temperature increases to 50° and spontaneous crystallization takes place. After two hours the crystallizate is separated with a suction filter and washed with DMF. The substance is chromatographically pure.
Yield: 14.6 g.
M.P. 279° to 282° C.
MS: 348.

B. 1-(p-Acetamino-phenyl)-2,3-dimethyl-4-aminopyrazolone-5

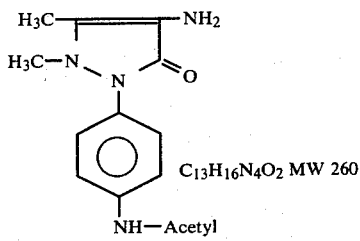

C₁₃H₁₆N₄O₂ MW 260

NH—Acetyl 10.0 g of the product of step A is dissolved in 350 ml of hydrochloric acid (2 N) at room temperature and then cooled to 10° C., whereupon the cleavage of the benzal compound takes place, which is complete within one hour. The acid solution is extracted with chloroform to remove the benzaldehyde. Then the pH is adjusted to 10.0 to 11.0 with soda lye at room temperature, and the alkaline solution is saturated with NaCl. Then follows another extraction with chloroform. The chloroform is withdrawn in vacuo. Residue: 6.1 g. This is recrystallized from 36 ml of ethanol.
Yield: 3.6 g.
M.P. 210° C. (Z).
MS: 260.
Chromatographically pure.

EXAMPLE 4

1-(Amino-p-tolyl)-2,3-dimethyl-4-amino-pyrazolone-5

The synthesis is performed in accordance with the following scheme:

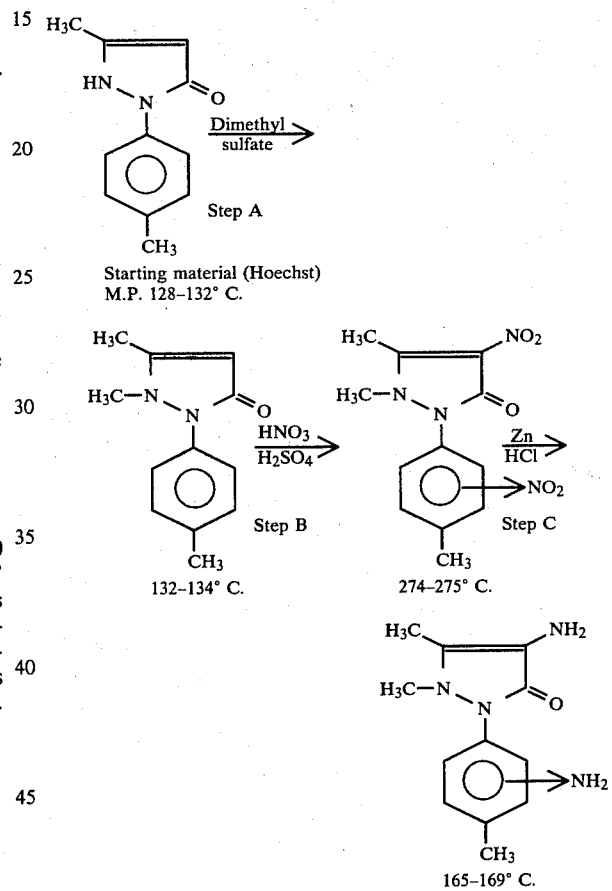

A. 1-(p-Tolyl)-2,3-dimethyl-pyrazolone-5

18.8 g of 1-(p-tolyl)-3-methyl-pyrazolone-5 is partially melted at 110° to 115° C., and 10.5 ml of dimethyl sulfate (0.11 mol) is added drop by drop over a period of 30 minutes. Then the mixture is heated at 170° C. for 5 hours. After cooling the mixture below 100° C., 35 ml of water is added. Then the mixture is refluxed for another 5 hours. After the mixture is cooled to 30° C., 25 ml of soda lye (33%) is added. pH = 10.0 to 11.0.

The mixture is again stirred for 5 hours at 90° to 95° C. Then it is cooled to room temperature and extracted four times with 100 ml of chloroform each time. The chloroform is withdrawn by distillation in vacuo.
Residue: 19.9 g.
M.P. 132°–134° C.
MS: 202.
DC Results: Uniform [=chromatographically pure.]

B. Dinitro compound of 1-(p-tolyl)-2,3-dimethylpyrazolone-5

10.73 g of the product of step A is added at 25° C. to 60 ml of concentrated sulfuric acid. Then a nitrating mixture of 8.05 ml of nitric acid (65%) and 12 ml of concentrated sulfuric acid is added drop by drop over a period of two hours with ice cooling. The temperature is to be from 5° to 7° C. After that the mixture is stirred for 30 minutes at room temperature and heated for an additional 30 minutes at 100° C.

After the solution has cooled to room temperature it is poured onto 0.5 kg of ice. After one more hour the crystallizate is separated with a suction filter and recrystallized from 280 ml of glacial acetic acid.

Yield: 11.5 g.
M.P. 274°–275° C.
MS: 292.

C. 1-Amino-p-tolyl)-2,3-dimethyl-4-aminopyrazolone-5

10.3 g of the product of step B is dissolved in 95 ml of concentrated hydrochloric acid at room temperature. 30 g of zinc dust is added, with stirring, at between 5 and 25° C. (icewater cooling), over a period of 1.5 hours until the solution is decolorized. Then 20 g of soda plus a total of 45 g of caustic soda flakes is added. The pH is to be higher than 10.0.

The thick mixture is dried at 40° C. in the vacuum dryer. The dry residue is pulverized and then extracted with chloroform for three hours. Residue: 7.47 g. Recrystallization is performed from 27.5 ml of ethanol.

Yield: 4.0 g.
M.P. 165°–169° C.
MS: 232.
DC Results: Uniform [=chromatographically pure.]

EXAMPLE 5

1-(o-Ethyl-amino-phenyl)-2,3-dimethyl-4-amino-pyrazolone-5

The synthesis is performed in accordance with the following reaction program:

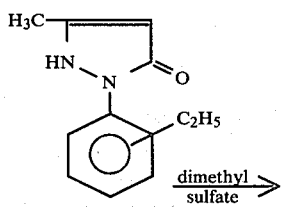

Step A
Starting material (Hoechst)
M.P. 128–130° C.

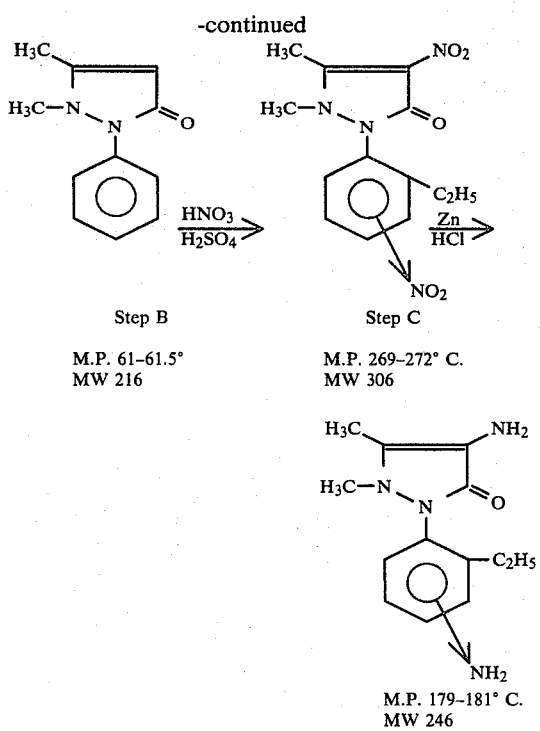

Step B
M.P. 61–61.5°
MW 216

Step C
M.P. 269–272° C.
MW 306

M.P. 179–181° C.
MW 246

A. 1-(o-Ethyl-phenyl)-2,3-dimethyl-pyrazolone-5

The methylation in the second position is performed as described in Example 4A.

Input:
20.2 g of 1-(o-ethyl-phenyl)-3-methyl-pyrazolone-5 (0.1 mol), 10.5 ml dimethylsulfate (0.11 mol). The substance becomes solid upon heating at 170° C. (5 hours). The amount of water required for dissolution is 60 ml. Residue after chloroform extraction: 20.4 g. Purification is performed on a silica gel column.

Yield: 16.7 g.
M.P. 61°–61.5° C.
MS: 216.
Chromatographically pure.

B. Dinitro compound of 1-(o-ethyl-phenyl)-2,3-dimethyl-pyrazolone-5

The nitration was performed as described in Example 4B.

Input:
11.47 g 1-(o-ethyl-phenyl)-2,3-dimethyl-pyrazolone-5.
60 ml sulfuric acid (conc.)

| | |
|---|---|
| 8.05 ml nitric acid (65%) | nitrating mixture |
| 12 ml sulfuric acid (conc.) | |

Residue: 14.7 g.
The recrystallization was performed from glacial acetic acid (390 ml).
Yield: 11.07 g.
M.P. 269°–272° C.
MS: 306.

C.
1-(o-Ethylaminophenyl)-2,3-dimethyl-4-amino-pyrazolone-5

The reduction of the dinitro compound was performed as described in Example 4C.
Input:
- 10.8 g dinitro compound,
- 235 ml hydrochloric acid,
- 36.5 g zinc dust.
- 20 g soda.
- 100 g caustic soda flakes.

Chloroform residue: 7.7 g.

Reprecipitation from chloroform/diisopropyl ether. For this purpose 6.0 g of the residue is dissolved in 140 ml of chloroform and then precipitated with 200 ml of diisopropyl ether.

Yield: 5.3 g.
M.P. 179°–181° C.
MS: 246.
DC Results: Uniform [=chromatographically pure.]

EXAMPLE 6

Determination of hydrogen peroxide formation in the oxidation of glycerin by glycerinoxidase.

Two reagents are prepared:
Reagent 1:
- 0.1 mol/l triethanolamine/HCl buffer, pH 8.0
- 3.6 mmol/l or 2 g/l isotridecyl ether
- 4.7 mmol/l or 2 g/l sodium cholate
- 10 mmol/l p-chlorophenol
- 0.5 mmol/l amino-substituted 4-aminoantipyrin
- 10 U/ml peroxidase Reagent 2: 500 U/ml glycerinoxidase For the performance of the determination, 2 ml of reagent 1 and 0.2 ml of reagent 2 were pipetted into a colorimeter cell. The extinction $E_1$ is read on the light meter at 546 nm. Then the reaction is started by the addition of 20 microliters of sample. After 20 minutes of reaction, the extinction $E_2$ is read. The incubation temperature is 25° C.

The evaluation is performed on the basis of a straight calibration line at which the measured extinction difference $\Delta E = E_2 - E_1$ of a standard solution of glycerin is related to the glycerin concentration.

The concentrations in the test solution are:
- 0.09 mol/l triethanolamine/HCl buffer, pH 8.0;
- 1.8 g/l (3.2 mmol/l) isotridecyl ether;
- 4.3 mmol/l sodium cholate;
- 9 mmol/l p-chlorophenol;
- 0.45 mmol/l aminosubstituted 4-aminoantipyrine;
- 9 U/ml peroxidase 45 U/ml glycerinoxidase.

EXAMPLE 7

The color stability of five compounds in accordance with the invention was tested. 4-Aminoantipyrin and sulfonated 4-aminoantipyrin were used as compounds for comparison.

With these standard compounds and the new compounds, the extinction $\epsilon$, the stability of the dye formed and $\lambda_{max}$ were determined, using p-chlorophenol, 2,4-dichlorophenol and ethylhydroxytoluidine (sulfonated) as phenolic couplers. The test system consisted of $H_2O_2$/POD/dye components.

Performance of the test:

The following reagents were used:
Reagent 1:
- 0.1 mol/l potassium phosphate buffer, pH 8.0
- 0.1 mmol/l 4-aminoantipyrin derivative
- 1.0 mmol/l phenol component
- 2 U/ml POD Reagent 2:
- 0.01 mol/l hydrogen peroxide solution.

Sample for determination:

Measuring radiation: Hg 546 nm; depth of substance in the cell: 1 cm; incubation temperature: room temperature.

2.0 ml of reagent 1 is pipetted into the cell, 10 microliters of reagent 2 (sample) are added and mixed. The extinction is traced for 70 minutes. A blank value is determined for each test, adding buffer instead of the hydrogen peroxide solution to reagent 1.

The results are summarized in the table below. The stated percentage of color stability (60 minutes at room temperature) relates to the difference which is produced by hydrogen peroxide with respect to the measuring signal. From the table it can be seen that $\lambda_{max}$ is negligibly affected by the new compounds of the invention, as is also the $\epsilon$ value. The new compounds of the invention are decidedly superior in color stability to the standards used for comparison.

TABLE

| Phenolic coupler | Compounds Used for Comparison | | Compounds Used in Accordance with the Invention | | | | |
| --- | --- | --- | --- | --- | --- | --- | --- |
| | 4-amino-antipyrin | 4-amino-antipyrin (sulfonated) | 4-amino-antipyrin | 1-(o-ethyl-aminophenyl)-2,3-dimethyl-4-aminopyrazolone-(5) | 1-(p-acet-aminophenyl)-2,3-dimethyl-4-aminopyrazolone-(5) | 1-(amino-p-tolyl)-2,3-dimethyl-4-aminopyrazolone-(5) | 1-(p-diethyl-aminophenyl)-2,3-dimethyl-4-aminopyrazolone-(5) |
| p-chlorophenol ($cm^2/\mu mol$) | 12 | 12 | 14 | 9 | 19 | 20 | 19 |
| color stability | +5% | +4% | +1% | +0% | +0% | +0% | +1% |
| max | 500 | 502 | 505 | 503 | 502 | 503 | |
| 2,4-dichlorophenol ($cm^2/\mu mol$) | 10 | 18 | 27 | 25 | 22 | 15 | 41 |
| color stability 505 | +2% | +7% | +1% | −1% | ±0% | +2% | +1% |
| max | | 507 | 508 | 507 | 508 | 502 | |
| Ethylhydroxy-toluidine (sulfonated) ($cm^2/\mu mol$) | 33 | 32 | 36 | 23 | 25 | 25 | 37 |
| color stability | +16% | −11% | −2% | −3% | −7% | −5% | −4% |
| max | 550 | 546 | 550 | 438 | 546 | 550 | 546 |

I claim:
1. A compound of the formula

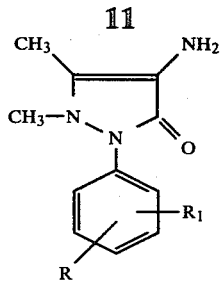
wherein R represents the group $N(R_2)_2$, in which each $R_2$ is an alkyl group of 1 to 3 carbon atoms, or one $R_2$ is an acyl group of 1 to 3 and the other $R_2$ is an alkyl group of 1 to 3 carbon atoms, and $R_1$ has the same meaning as R or is a hydrogen atom or $NH_2$.
2. Compound of claim 1, wherein $R=NH_2$ and $R_1=H$.
3. Compound of claim 1 wherein R is $N(R_2)_2$ in which $R_2$ is an alkyl group of 1 to 3 carbon atoms.
* * * * *